United States Patent [19]

Pitha

[11] Patent Number: 5,681,828
[45] Date of Patent: Oct. 28, 1997

[54] SELECTIVE ALKYLATIONS OF CYCLODEXTRINS LEADING TO DERIVATIVES WHICH HAVE A RIGIDLY EXTENDED CAVITY

[76] Inventor: Josef Pitha, 417 S. Anglesea St., Baltimore, Md. 21224

[21] Appl. No.: 575,075

[22] Filed: Dec. 19, 1995

[51] Int. Cl.$^6$ .................. A61K 31/715; A01N 43/04; C08B 37/16; C07H 1/00
[52] U.S. Cl. .................. 514/58; 536/103; 536/124
[58] Field of Search .................. 536/103, 124; 514/58

[56] References Cited

U.S. PATENT DOCUMENTS 4,764,604  8/1988  Müller .................. 536/103

FOREIGN PATENT DOCUMENTS 197571  3/1985  European Pat. Off. .
646602  4/1995  European Pat. Off. .
62-059601  3/1987  Japan .

*Primary Examiner*—John Kight
*Assistant Examiner*—Everett White
*Attorney, Agent, or Firm*—Glenna Hendricks; Stephen Gates

[57] ABSTRACT

By controlling basicity of the reaction, it is possible to alkylate preferentially the secondary hydroxyls of cyclodextrins. These hydroxyls surround the principal, wide, entry into the cyclodextrin cavity and, thus, their substitution by suitably chosen substituents can improve the formation of inclusion complexes. By methods of the invention, cyclodextrin derivatives substituted with fused 1,4-dioxane ring (s) can be obtained. If a reagent with one alkylating moiety is used, a mixture of ethers of cyclodextrin is formed. Using methods of this invention, up to 96% of the substitution can be directed to the secondary hydroxyls.

5 Claims, No Drawings

SELECTIVE ALKYLATIONS OF CYCLODEXTRINS LEADING TO DERIVATIVES WHICH HAVE A RIGIDLY EXTENDED CAVITY

FIELD OF THE INVENTION

This invention is related to previously unknown cyclodextrins and methods of making and using compositions containing such cyclodextrins. The cyclodextrin compositions of the present invention make it possible to solubilize and stabilize larger molecules such as peptides.

BACKGROUND OF THE INVENTION

For solubilization of non-polar compounds, either organic solvents or detergents are routinely used. Water soluble compounds wherein molecules form a cavity into which non-polar compounds can be included can be used instead of solvents and detergents.

Cyclodextrins are a group of cyclic oligosaccharides in which glucopyranosyl residues are joined by alpha (1 to 4) glycoside linkages, the same linkages which are prevalent in starch, from which cyclodextrins are made by enzymatic means. There are two secondary and one primary hydroxyls per glucopyranosyl residue. Three of cyclodextrins are of particular interest: alpha-, beta and gamma-, which have respectively six, seven or eight gluco-pyranosyl residues. Since each of the glucopyranosyl residues has two secondary and one primary hydroxyls, alpha-, beta and gamma-cyclodextrins have respectively 18, 21 or 24 hydroxyls, any of which can be alkylated.

Use of cyclodextrins presents a number of health and environmental advantages. However, full utilization is hampered by cyclodextrins' relatively low solubilizing potency. Consequently, methods to improve solubilization potency are needed. Chemical modifications of alpha-, beta- and gamma-cyclodextrins which have the potential to improve their ability to form inclusion complexes, and thus, solubilize non-polar compounds into polar solutions are described herein. The same chemical modifications can also be used in preparation of water insoluble derivatives of cyclodextrins for selective absorption of non-polar compounds from polar solutions.

For purposes of this description, the term "alkylating reagent" is understood to mean a reagent which, in the course of its reaction (termed "alkylation") liberates a strong acid; for example, alkylation of cyclodextrin with epichlorohydrin is accompanied by the release of hydrochloric acid.

Three aspects of previous art in derivatization of cyclodextrin should be considered. The first aspect concerns the bases used in alkylations, the amounts used and the method of introduction of these bases into the reaction mixture. Bases have multiple roles in alkylations. To alkylate any carbohydrate, a base is required since alkylating reagents react with acceptable rates only with the anions of carbohydrates; thus, there must be enough of base to form salts from carbohydrates, which have rather low acidity. As the alkylation proceeds, a strong acid is liberated from the alkylating reagent and this acid must be neutralized by the base present for the alkylation to proceed. Bases have two other roles in the alkylations—they speed the dissolution of cyclodextrins and the decomposition of excess toxic alkylating agents after the reaction is finished. Consequently, large quantities of bases at high concentration have been used. In contrast to the previous art, this invention delineates the advantages of performing the alkylations with only a minimum of base present in the reaction mixture at any moment when the alkylation takes place.

Secondly, the prior art teaches use of reagents which have two alkylating moieties per molecule, for example, epichlorohydrin, only for purposes of preparing either water insoluble cyclodextrin resins or water soluble cyclodextrin polymers. The latter were as effective in pharmaceutical applications as hydroxypropyl cyclodextrins (compare, for example, U.S. Pat. No. 4,596,795), but since they could not be satisfactorily characterized, they have not been used. While some monomers may have been present in the mixtures produced, method for selective production of monomers was not previously known.

Finally, it is interesting, in studying the prior art, to note the lack of instruction regarding control of the reaction products obtained from alkylation of cyclodextrins with reagents having two alkylating moieties. Using the novel method disclosed herein, a structural element not previously detected in the prior art is formed.

The reaction of cyclodextrins with epichlorohydrin was used by Wiedenhof et al. to prepare and study products called "water soluble E-resins of alpha- and beta-cyclodextrins." Aqueous sodium hydroxide of concentrations 12% and 9.8% were used in preparation. On the basis of analyses (chemical, infrared spectra and nuclear magnetic resonance spectra), Wiedenhof et al. proposed that water soluble polymers contain the following structural elements: (a) "bridges" connecting different cyclodextrin residues in the polymeric network of the structure O—$CH_2$—CHOH—$CH_2$—O and (b) "tails" and "polytails" on terminuses of the network which have the respective structures O—$CH_2$—CHOH—$CH_2OH$ and (O—$CH_2$—CHOH—$CH_2$)$_n$—O—$CH_2$—CHOH—$CH_2OH$. Fenyvesi et al., when evaluating materials prepared similarly, also found only these structural elements present; furthermore, the prior art indicated that some of the products had to contain some monomer just modified by the "tails and polytails." The same materials were evaluated later by Suzuki et al. using $^{13}C$ nuclear magnetic resonance spectra. Again, only the above listed structural elements were detected. Methods for preparation of water soluble cyclodextrin polymers were later modified by Szejtli who used a mixture of aqueous sodium hydroxide and strong anion exchange resin in place of plain aqueous sodium hydroxide. The resulting compounds were described as polymeric in character.

The reaction of epichlorohydrin with cyclodextrins leading to water insoluble products was, following the common practice, accomplished using concentrated aqueous sodium hydroxide as a base. Thus, for example, in JP 58171404 the starting concentration of NaOH was 24%, in JP 60020924 the concentration of NaOH was 28% and in JP 57130914 the concentration of NaOH was 15%.

No records of reaction of cyclodextrins with 1,2-dichloroethane or similar vicinal dihalides were found.

It also has been common practice, when alkylating cyclodextrins with alkylating reagents having one alkylating group, to use strongly basic solutions. For example, in alkylation of beta-cyclodextrin with sultones described in U.S. Pat. No. 5,134,127, the concentration of sodium hydroxide in the reaction mixtures was recommended to be, "set at a level higher than 10% (wt/wt), preferably in the range of 40-60% (wt/wt)." Products of the reaction contained some starting cyclodextrin, which had to be removed by purification. The importance of moderating the basicity of reaction mixtures when cyclodextrins were alkylated by reagents with one alkylating moiety was established for aqueous media by Pitha et al. and for the anhydrous media by Rong et al., both references of 1990. Compare also U.S. Pat. No. 5,096,893. Reuben et al. and Jindrich et al. were also aware of some of the advantages of moderating the basicity and used the lowest recorded concentrations of sodium hydroxide (1.5%) in water in alkylations of beta-cyclodextrin with chloroacetic acid and alkyl halogenides, respectively. In experiments of Rong et al., Reuben et al. and Jindrich et al., the basicity was controlled by dilution of the base with solvent. Basicity decreased as the reaction progressed. No attempts to keep basicity constant throughout the reaction period were found. European patent publication 0 646 602 A1 of Wimmer teaches and claims methods of reacting cyclodextrins with alkylating agents by a method wherein the cyclodextrins are dissolved in part in base and thereafter the alkylating agent and the base are added. The processes differ from the present invention in that the basicity is essentially uncontrolled.

Holmberg et al. teaches new structural elements in Sephades G 25, which is a water insoluble resin formed from dextran by crosslinking with epichlorohydrin in 10% sodium hydroxide. Dextran is a branched polysaccharide in which glucopyranosyl residues are linked predominantly by alpha (1 to 6) glycoside linkages, and thus, dextran is substantially different structurally from cyclodextrins, in which six, seven or eight glucopyranosyl residues are linked by alpha (1 to 4) glycoside linkage in alpha-, beta- or gamma-cyclodextrins, respectively. The difference in glycoside linkage results in dextran having three secondary hydroxyls.

SUMMARY OF THE INVENTION

It is the purpose of this invention to provide new cyclodextrins having substituents that enhance usefulness of the cyclodextrins. Similar cyclic structures were detected only recently in derivatives of other carbohydrates. Using the methods of the invention, it is possible to form fused 1, 4-dioxane rings on cyclodextrins.

This invention provides means for directing selective of alkylation of cyclodextrins whereby hydroxy groups of carbohydrates are dissociated by a base to alkoxide anions for alkylation. By minimizing the kind and number of reactive anions of cyclodextrins, intramolecular reactions are favored over intermolecular reactions. This results in preparation of cyclodextrins with intramolecular rather than intermolecular crosslinkings.

If an alkylating reagent with one alkylating moiety is used a mixture of ethers of cyclodextrin is formed. (Nevertheless, except for presence of many isomeric and homologous ethers, there are no further chemical complications. If a reagent with two alkylating moieties is used (as for example 1,2-dichloroethane) the product of the first step is the same. A mixture of many simple ethers is formed but each of the substituents thus introduced carries an additional alkylating moiety. This cyclodextrin attached alkylating moiety can then, in the second step of the reaction, follow one of three pathways:

(1) A simple hydrolysis of the second alkylating moiety can take place and the corresponding hydroxyalkyl ether of cyclodextrin is thus formed.

(2) The second alkylating moiety can alkylate another cyclodextrin and thus two cyclodextrins become connected by a linker, to form dimers. Consequently this process can be called intermolecular crosslinking. If crosslinking continues, water soluble polymers or water insoluble resins are formed.

(3) The second alkylating moiety can alkylate another hydroxyl of the same cyclodextrin. This process can be called intramolecular cross-linking. If intramolecular crosslinking occurs between two secondary hydroxyls of glucopyranosyl residue, a new six member 1,4-dioxane ring is formed which is fused to the glucopyranosyl residue.

The conformationally rigid cavity in cyclodextrin molecules makes possible the formation of inclusion complexes with other molecules which are held within the cavity. The invention provides means of enhancing the ability of cyclodextrins to form inclusion complexes. The cyclodextrins of the invention have enhanced solubilization potential because of the enlargement of the rigid cavity, since the cavity is, by methods of the invention, extended in a conformationally rigid manner—as for example by fusion of dioxane rings to the rim of the cavity. The methods of the invention can be implemented easily and at little expense.

By methods of the invention, it is possible to obtain substituted cyclodextrins wherein no more than 30% of the mixture is dimmer and at least 70% of the mixture is monomer with at least 10% of the cyclodextrins having the cyclic dioxane moiety. It is possible to obtain compositions wherein up to 60% of the substituted cyclodextrins have the cyclic dioxane moiety which enlarges the cavity.

DETAILED DESCRIPTION OF THE INVENTION

By the novel methods of the invention, alkylation of cyclodextrins is performed in media which has a minimal basicity needed to sustain an acceptable reaction rate. When such conditions are used, the reaction products have simpler structures and are better suited to form inclusion complexes than when the products are made under conditions of high basicity. The following is an example of one of many reactions which can occur using the methods of the invention:

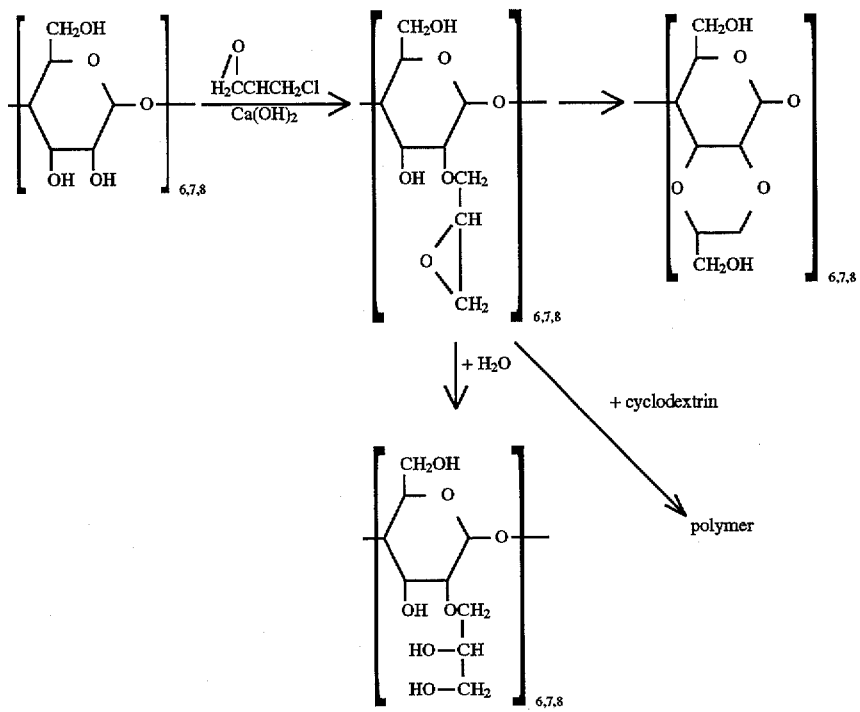

The moieties having the dioxane ring may be substituted in the following manner:

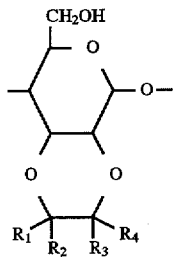

wherein $R_1$, $R_2$ $R_3$, and $R_4$ may be H, alkyl of 1–3 carbon wherein the alkyl may have a hydroxy substituent with the provision that at least two of $R_1$, $R_2$ $R_3$, and $R_4$ are hydrogen and no more than one of $R_1$, $R_2$ $R_3$, and $R_4$ is hydroxyalkyl. If two of $R_1$, $R_2$ $R_3$, and $R_4$ is substituted by alkyl, both alkyl's will be on the same ring carbon. Examples are 2-methyl-1,4-dioxane, 2-hydroxymethyl-1,4-dioxane and 2,2 dimethyl-1,4-dioxane moieties.

Advantages of Minimal Basicity

Alkylation of cyclodextrins occur at reasonable rates only when the basicity of the reaction mixture is sufficient to cause cyclodextrins begin to dissociate significantly to cyclodextrin anions. Thereafter, the alkylation may proceed rapidly. Hydrolysis of the alkylating reagents (which inevitably occurs in aqueous media and wastes the reagent) also occurs as a result of alkylation of hydroxide anions under sufficiently basic conditions. Since cyclodextrins are dissociated to anions more easily (pKa 12.3, 12.2 and 12.1 for alpha-, beta- and gamma-cyclodextrins, respectively as measured by Gelb et al.) than water (pKa 15.7), an appropriate choice of basicity may diminish this waste. Furthermore, use of minimal basicity makes it possible to control alkylations in order to obtain specific products of the reaction. (Gelb et al. suggests that anions of cyclodextrins are formed mainly through ionization of the secondary hydroxyls.) Some of the alkylations routinely used on cyclodextrins introduce substituents containing new hydroxy groups (for example 3-hydroxypropyl) which themselves can be alkylated as the reaction proceeds. Keeping the basicity minimal can diminish even this side reaction, since acidity of non-activated alcohols (pKa values 15.9–18) is lower than that of cyclodextrins.

Methods to Control to Minimize Basicity

It is sometimes possible to control (minimize) basicity by dissolution of cyclodextrin and all, or part of the alkylating reagent in a suitable solvent followed by gradual addition of base. If the rate of addition is slower than the rate of reaction (and base consumption), the reaction occurs close to the conditions of minimal basicity. The alkylation rates of reagents investigated decreased in the order epichlorohydrin>methyl iodide>3-chloro-2-methylpropene>1,2-dichloroethane. This method worked well when the alkylating agent was epichlorohydrin, as shown in Example 7. The utilization of the alkylating reagent was better than that in the control experiment described in Example 6, in which the routine procedure was used wherein cyclodextrin was dissolved in the solution of base followed by slow addition of epichlorohydrin.

A second method depends on the use of bases of limited solubility. Calcium hydroxide dissolves at room temperature only to the concentration of 0.022M (pH 12.4) and at 100° C. to a rate of 0,009M. The basicity obtained using this reagent was satisfactory to keep rates of alkylations of cyclodextrins in an acceptable range. When calcium hydroxide is used (Examples 1–5 and 9–19), the processes are occasionally complicated by formation of precipitates or gels (Examples 5 and 17–19). Thus, for example, at room temperature a gel was formed upon addition of calcium hydroxide to the solution of gamma-cyclodextrin (Example 5). This gel was stiff enough to prevent stirring. Alkylation of this gel, nevertheless, could be performed in a ball mill and liquefaction occurred within an hour of rotation when epichlorohydrin was used (Example 5). The formation of the gel could be completely prevented by an increase in temperature and the alkylation could then be performed using a magnet driven stirrer (Example 2). When alpha-cyclodextrin was used, formation of gels was observed only when concentrated solutions were used (Example 14). With beta-cyclodextrin, gels were not detected. Thus, while replacement of the usually used sodium hydroxide with a cheaper and environmentally friendly calcium hydroxide may lead to complications, the resulting difficulties can easily be resolved.

Alternative methods for use of calcium hydroxide were tested —precipitation of calcium or magnesium hydroxide in situ by a gradual addition of sodium hydroxide to an assembled reaction mixture containing cyclodextrin, alkylating agent, and water soluble calcium or magnesium salts (Example 8). These modifications were found to work, but no clear advantage over the use of calcium hydroxide was detected.

In another alternative method, the basicity of reaction mixtures was regulated using the buffering capacity of alkali aluminates, zincates or silicates (Example 8). These salts are soluble in aqueous media and act as pH buffering agents. When the pH of the mixtures decreases, hydrated oxides precipitate. While these processes were acceptable, no clear advantage over the use of calcium hydroxide was detected.

Alkylating Reagents and Products

Use of the above procedures in alkylation of cyclodextrins with epichlorohydrin is described in Example 1. Analysis of products by mass spectrometry indicated that decreasing the basicity of the reaction mixtures resulted in substitutions occurring predominantly on the secondary hydroxyls. The reactions occurred in a very uniform manner. That the substitution occurred predominantly on the secondary hydroxyls is evidenced by a high content in the products of species which have fused 1,4-dioxane rings to the 2- and 3-positions of glucopyranosyl residues. These species were not previously detected in cyclodextrin derivatives. To form such species, the substitution must occur on the secondary hydroxyl which has a free hydroxyl group as a neighbor, since substitution must be followed by an intramolecular cyclization involving the neighboring free secondary hydroxyl. Not all substitutions on secondary hydroxyls end in the formation of fused 1,4-dioxane rings. If a reaction with water instead of the intramolecular cyclization occurs, the product contains cyclodextrins with 2,3-dihydroxypropyl substituents. Nevertheless, conditions of minimal basicity enable preparation of mixtures in which fused 1,4-dioxane rings represent the majority of the substitutions introduced.

That the alkylation at minimal basicity occurred in a uniform manner can be documented by comparison of the number of substituents per molecule when different amounts of epichlorohydrin were used in the reaction (Examples 1 and 2). The number of substituents per molecule and amount of high molecular weight fraction in products increased in proportion to the amount of epichlorohydrin used. Furthermore, the average molecular weight of components of products made under the specific conditions of "high substitution" in Examples 2–4 could be correlated with the number of glucopyranosyl residues per molecule. The correlation was linear and the average molecular weight increased by 207 mass units per the residue over the range evaluated—that is, from six to sixteen glucopyranosyls and from 1200 to 3300 mass units. Such regularities can be expected when the predominant substitutions occur with comparable rates and the system is not kinetically biased towards polymerization.

Vicinal dihalides were used to alkylate cyclodextrins in Examples 9–14. The 1,2-dichloroethane is relatively unreactive (note, this compound and 1,2 dichloropropane have been used as an inert dry cleaning solvent); nevertheless, a product containing fused 1,4-dioxane residues was obtained just by a refluxing at normal pressure and without any activation (Example 9). An activator was used in Example 10. Use of pressure vessels is bound to provide further improvement in results. This process may have advantage over others used in the cyclodextrin field for safety reasons. 1,2-Dichloroethane is less toxic than either epichlorohydrin or propylene oxide and less volatile and easier to handle than the latter. Other tested compounds were 1,2-dibromopropane (Example 13) and 1,2-diiodoethane. The former yielded derivatives containing fused 2-methyl-1,4-dioxane rings. The diiodoethane gave the same products as 1,2-dichloroethane. The reaction with 1,2-dichloro-ethane was also performed with success in anhydrous medium (Example 14).

The use of reagents with one alkylating moiety was examined using methyl iodide (Example 15), 3-chloro-2-methylpropene (Example 16), 1,3-propanesultone (Example 18), diethylaminoethyl chloride (Example 17) and acetanhydride (Example 19). All of these gave the expected products of quality equal or superior to those obtained by other methods. In these reactions, as in the reactions described above, one can expect that the substitution occurs preferentially (but not entirely) on secondary hydroxyls. This expectation is supported by the results of the experiment in which the products of alkylation of gamma cyclodextrin with 3-chloro-2-methylpropene (Example 16) were treated with an anhydrous acid (Example 19). The alkylation yields 2-methylpropen-3-yl ethers, which, by acid catalysis, undergo an intramolecular cyclization to gamma cyclodextrin derivatives containing fused 2,2-methyl-1,4-dioxane rings. This type of cyclization is possible only if the alkylation occurred on one of the secondary hydroxyls of the glucopyranosyl residues of gamma-cyclodextrin. In alkylations using 1,3-propanesultone (Example 18), the advantage of the present process over the prior art methods is obvious. The product did not contain any starting material, and thus, no special purification processes such as those described in U.S. Pat. No. 5,134,127, were necessary.

The reason the above processes give better products than those obtained by alkylation of cyclodextrins at high basicity, whether reagents with one or two alkylating moieties are used, can be attributed to several factors. When strongly alkaline media are used, the reaction mixture soon after initiation contains a large variety of anions. Some of these anions are formed from the already derivatized starting material. Some of these anions will react rapidly with alkylating agents and compete with the starting material, which may remain unreacted. Furthermore, these reactive anions may prevent formation of fused 1,4-dioxane rings since intermolecular reactions may be competitively favored over the intramolecular cyclizations. Lowering the basicity of the reaction media decreases the variety and number of anions present, and thus, decreases the probability that some extraordinary reactive intermediary species will be present. Consequently, products will contain less of the staring material and of polymeric species and more of compounds formed by intramolecular cyclization.

Cyclodextrin derivatives, in addition to solubilization purposes, have been used to absorb selectively some compounds from gases or from polar solutions. For these insoluble, resin-type applications, derivatives are important. The products containing fused 1,4-dioxane rings would provide advantages since they bind and absorb compounds more efficiently. Consequently, insoluble resins in which the presence of 1,4-dioxane rings fused to cyclodextrin are unequivocally present were made. These compounds were obtained by crosslinking with epichlorohydrin products in which these rings were present could be documented by mass spectrometry (Example 21). Obviously, resins of a similar type can also be made by a direct one-step process in which concentrated solutions of alpha-, beta-, or gamma-cyclodextrins are reacted with epichlorohydrin in conditions of controlled, moderate basicity. The procedures suitable for the solubilization and stabilization of substances with low water solubility using cyclodextrin derivatives are described in Example 22.

METHODS USED IN THE IDENTIFICATION OF PRODUCTS

Multicomponent mixtures of cyclodextrin derivatives can not be completely analyzed. Nevertheless, when the synthetic methods disclosed in this disclosure are used, the products are sufficiently simple that all structural elements in all major components can be determined. In contrast, the prior art methods yielded diverse products which could not be adequately characterized.

For the initial characterization and mutual comparison of products, thin layer chromatography was used. While multicomponent mixtures usually give continuous spots, results are similar only for the products of about the same type and degree of substitution. By thin layer chromatography unequivocal assessment of the products for the presence of the polymeric fractions is possible. Thin layer chromatographic analysis of the products was performed on precoated silica gel plates using 1-propanol-water-ethyl acetate - ammonium hydroxide (6:3:1:1) as a solvent for the developing process. The substances were revealed as blue spots by heating the plate after a brief dipping into a Vaugh's reagent (a solution of ceric sulfate, 1 g, ammonium molybdate, 24 g, in 10% sulfuric acid, 500 ml). This system effectively separates members of series in which the number of substituents increases (that is, the starting compound from monosubstituted, disubstituted and so on). An increase in the number of sterically exposed hydroxy groups in the molecule lowers the Rf value; an increase in the number of nonpolar groups increases Rf. Thus, substitutions with a dihydroxypropyl group lower the Rf value, while those with a methyl or with a fused 1,4-dioxane ring increase the Rf. Compounds with multiple cyclodextrin moieties per molecule, which have a large number of hydroxy groups per molecule, display low Rf, while polymers of cyclodextrins have Rf close to zero.

Distribution of molecular weight and determination of the type of substituents present were obtained from mass spectra. Only those regions of the spectra in which peaks of molecular ions appear were analyzed and, unless otherwise stated, peaks had to comprise more than 15% of the most intensive peak in the region (base peak) to be counted. In the first approximation, intensities of peaks observed in the molecular ions region are proportional to representation of the species of the particular molecular weight present in the sample. Mass spectra were measured either in FAB or MALDI modes. FAB mode was used in conjunction with glycerol—trifluoroacetic acid matrix which yields ions (M+H)+. FAB spectra may be somewhat complicated by the remnants of matrix elements (aggregates of glycerol) which escaped the intrinsic correction process; this complication decreases rapidly with the increasing molecular weight. MALDI mode yields predominantly (M+Na)+ ions and for calculations molecular weights m/z values had to be corrected for the mass of sodium.

The following conventions were used to describe mass spectra in the region of molecular ions. At first the mass of the peak— m/z—is given. This is followed by its relative intensity, expressed as a percentage of the most intensive peak (base peak) of the region. Then attribution of the peak is made by enumeration of groups substituting the cyclodextrin ring. Each of the attributions is enclosed by parentheses. A substitution of two secondary hydroxyls of a cyclodextrin by the groups —CH$_2$—CH$_2$— or —CH(CH$_3$) —CH$_2$— or —C(CH$_3$)$_2$—CH$_2$— was denoted by a letter D (for dioxane), preceded by the number of the groups present. A substitution by 2.3-dihydroxypropyl group was denoted similarly, but by a letter G for glycol. Thus, a cyclodextrin species carrying two fused dioxane rings and one dihydroxypropyl unit will be denoted as 2D1G. Names of other groups in attribution statements were not abbreviated. At low substitution, each peak observed can be attributed to just one species. At higher substitutions, certain species have very close m/z values. For example, 3G has m/z 1519 and 4D has m/z 1521. Consequently, both these components may contribute to the same peak. To stress this equivocality, the attribution of the peak close to m/z 1520 is made to 3G and 4D species. To compare how various conditions favor formation of 1,4-dioxane rings, a "ring favoring ratio" is given in which intensities of peaks of species differing by just one ring closure are compared (for example, intensity of 3D1G peak divided by that of 2D2G peak).

EXAMPLE 1

Alkylation by epichlorohydrin of gamma-cyclodextrin in refluxing suspension of calcium hydroxide resulting in low degree of substitution:

Gamma-cyclodextrin (10 g of hydrate, 55 mmoles of glucopyranosyl residue) was dissolved in water (200 mL), contained in an Erlenmayer flask equipped with reflux condenser and placed on a heater-magnetic stirrer plate. While stirring, calcium hydroxide (2.32 g, about 31m moles) was rapidly added and heating started. A transient thickening of the suspension through gel formation may be observed, but the gel is completely dissociated as the temperature increases. When the reflux temperature was reached, epichlorohydrin (4.4 ml, 56 mmoles) was added drop-wise in 10 minutes through the reflux condenser. Stirring and heating were continued for another 75 minutes; at this point no epichlorohydrin is detectable in the sample of the condensate and, optionally, volume can be reduced by distilling some water off. The reaction mixture was left to cool to room temperature and filtered to get rid of the remaining calcium hydroxide; in other experiments, decantation was used instead. The filtrate at this point may not be completely clear. At this point, it is advantageous to adjust the pH to 6 by acetic acid. This adjustment results in a complete clarification and prevents precipitation of calcium carbonate during the subsequent dialysis. The solution was then dialyzed three times against water and filtered again; the addition of powdered cellulose at this point helps to clarify the filtrate, which then was evaporated in vacuo to dryness. The glassy residue was scraped from the evaporating flask and ground to a white powder (7.965 g).

Upon chromatography analysis, the product formed a continuous spot with Rf 0.12–0.56 with stronger colorations at Rf 0.43, 0.36 and 0.31; gamma-cyclodextrin under the same condition had Rf 0.29.

Upon mass spectrometry analysis performed in MALDI mode, the following peaks were observed in the area of molecular ions of the components which have one cyclodextrin ring per molecule:

m/z 1387, 38%, (1D); m/z 1395, 21%, (1G); m/z 1433, 88%, (2D); m/z 1451, 84%, (1D1G); m/z 1470, 22%, (2G); m/z 1490, 58%. (3D): m/z 1507, 100%, (2D1G); m/z 1525, 60%, (1D2G); m/z 1545, 22%, (4D); m/z 1563, 44%, (3D1G); m/z 1581, 51%, (2D2G); m/z 1600, 21%, (1D3G); m/z 1638, 11%, (3D2G); m/z 1655, 15%, (2D3G) and (6D).

From the above data, the average molecular weight was calculated to be 1444. Only the last peak could not be unambiguously attributed to a single species containing stated structural elements. If this peak is not counted, the product contains 1.96 substituents per molecule and from these substituents 61% (by number) contain fused 1,4-dioxane rings. The peak of gamma-cyclodextrin was less than 5% of the base peak.

EXAMPLE 2

Alkylation by epichlorohydrin of gamma-cyclodextrin in refluxing aqueous suspension of calcium hydroxide; high degree of substitution:

Gamma-cyclodextrin (10 g of hydrate, 55 mmoles of glucopyranosyl residue) was dissolved in hot water (50 ml) and added to a stirred boiling suspension of calcium hydroxide (4.63 g, 62 mmoles in 50 ml of water). Then, through the reflux condenser, epichlorohydrin (8.8 ml, 111 mmoles) was added drop-wise in 10 minutes. Stirring and heating was continued for another 75 minutes and then the mixture was left to cool to room temperature and processed as described above. The glassy residue after evaporation was of slight yellow color and was ground to a white powder (8,043 g). The slight discoloration of the product is due to the isomerization and condensations of epichlorohydrin derived compounds during the alkaline condensation. It can be ameliorated by the addition of a small amount of sodium borohydride to the reaction mixture before epichlorohydrin is added.

Analysis of the product by chromatography revealed that polymeric components are absent. The product formed a continuous spot of Rf from 0.06 to 0.56; gamma-cyclodextrin, under the same conditions, had Rf 0.29.

When analysis by mass spectrometry was performed in FAB mode, the following peaks were observed in the area of molecular ions of components which have one cyclodextrin ring per molecule:

m/z 1466, 27%, (3D) and (matrix); m/z 1484, 20%, (2D1G); m/z 1503, 17%, (1D2G); m/z 1522, 53%, (3G) and (4D); m/z 1540, 72%, (3D1G); m/z 1558, 45%, (2D2G) and (matrix); m/z 1578, 44%, (1D3G) and (5D); m/z 1596, 94%, (4G) and (4D1G); m/z 1614, 100%, (3D2G); m/z 1632, 56%, (2D3G) and (6D); m/z 1652, 55%, (1D4G) and (5D1G) and (matrix); m/z 1670, 92%, (5G) and (4D2G); m/z 1688, 93%, (3D3G) and (7D); m/z 1708, 53%, (2D4G) and (6D1G); m/z 1726, 46%, (1D5G) and (5D2G); m/z 1744, 64%, (6G) and (4D3G) and (8D) and (matrix); m/z 1762, 62% (3D4G) and (7D1G); m/z 1782, 37%, (2D5G) and (6D2G); m/z 1800, 32%, (1D6G) and (5D3G); m/z 1818, 36%, (7G) and (4D4G) and (8D1G); m/z 1838, 34%, (3D5G) and (7D2G) and (matrix); m/z 1856, 36%, (2D6G) and (6D3G); m/z 1875, 18%, (1D7G) and (5D4G); m/z 1893, 19%, (8G) and (4D5G) and (8D2G); m/z 1912, 17% (3D6G) and (7D3G); m/z 1931, 15%, (2D7G) and (6D4G) and (matrix).

The average molecular weight was calculated to be 1671 and the half-width of the envelope of molecular weight distribution was about 270. Gamma-cyclodextrin was not detected. The majority of peaks could not be unequivocally attributed; therefore, the overall distribution of the substituents could not be calculated. That the above procedure favors the formation of 1,4-dioxane rings over the substitution with dihydroxypropyl substituents is possible to see from intensities of 3D1G and 2D2G peaks; the ring favoring ratio calculated using these is 1.02.

For an analysis of the product for species containing one and two cyclodextrin units, a spectrum in MALDI mode was recorded. The analysis of molecular ion region of components containing one cyclodextrin ring per molecule in this spectrum enabled a comparison of results obtained in FAB and MALDI modes. In MALDI mode, the average molecular weight was 1606 (sodium corrected) compared to the 1671 found by FAB above. In MALDI, the base peak (M+Na)+ was at m/z 1637, obviously the same component which formed the base peak (M+H)+ of 1614 in the FAB mode described above. In the region of molecular ions of components containing two cyclodextrin rings, the peaks and their attribution were as follows:

m/z 3097, 20%. (1D5G) and (5D2G); m/z 3117, 23%, (6G) and (4D3G) and (8D); m/z 3134, 28%, (3D4G) and (7D1G); m/z 4154, 32%, (2D5G) and (6D2G); m/z 3172, 43%, (1D6G) and (5D6G) and (9D); m/z 3191, 33%, (7G) and (8D1G) and (4D4G); m/z 3209, 43%, (3D5G) and (7D2G); m/z 3228, 79%, (2D6G); m/z 3246, 52%, (1D7G) and (5D4G) and (9D1G); m/z 3265, 53%, (6G) and (8D2G) and (4D5G); m/z 3283, 75%, (3D6G) and (7D3G); m/z 3302, 100%, (2D7G) and (6D4G) and (10D1G); m/z 3321, 78%, (1D8G) and (5D5G) and (9D2G); m/z 3339, 52%, (9G) and (8D3G) and (4D6G); m/z 3358, 88%, (3D7G) and (7D4G) and (11D1G); m/z 3376, 84%, (2D8G) and (6D5G) and (10D2G); m/z 3393, 83%, (1D9G) and (5D6G) and (9D3G); m/z 3413, 60%, (10G) and (4D7G) and (8D4G); m/z 3432, 66%, (3D8G) and (7D5G) and (11D2G); m/z 3449, 66%, (2D9G) and (6D6G) and (10D3G); m/z 3468, 46%, (1D10G) and (5D7G) and (9D4G); m/z 3486, 36%, (11G) and (4D8G); m/z 3505, 47%, (3D9G) and (7D6G); m/z 3526, 40%, (2D10G) and (6D7G) and (10D4G); m/z 3543, 34%, (1D11G) and (5D8G) and (9D5G); m/z 3564, 31%, (9D12G) and (4D9G) and (8D6G) and (12D3G) and (16D); m/z 3582, 28%, (3D10G) and (7D7G) and (11D4G) and (15D1G); m/z 3600, 23%, (2D11G) and (6D8G) and (10D5G) and (14D2G).

From the above data, the average molecular weight of components which contain two cyclodextrin units per molecule is 3348. For 100 molecules of components containing one cyclodextrin ring, there are 22 molecules of components containing two cyclodextrin rings. In other words, if the mixture is assumed to consist entirely from the components of one or two cyclodextrin rings per molecule, the former represent 68% by weight.

EXAMPLE 3

Alkylation by epichlorohydrin of beta-cyclodextrin in refluxing aqueous suspension of calcium hydroxide; high degree of substitution:

The same procedure as described above was used for beta-cyclodextrin and yielded 7.556 g of the product. Chromatographic analysis showed that no polymeric components were present. The product appeared as a continuous spot between Rf 0.11 to 0.58; beta-cyclodextrin on the same plate had Rf 0.33.

Upon analysis by mass spectrometry in FAB mode, the peaks enumerated below were observed in the area of the molecular ions of the components which have one cyclodextrin ring. Since the attribution (except of that for matrix) runs in parallel to that above (the attribution of the peak at m/z 1304 here corresponds to that at m/z 1466 in gamma cyclodextrin, that of at m/z 1322 to that of at m/z 1484 and so on) the attribution entries were omitted from the list below:

m/z 1304, 42%; m/z 1322, 42%; m/z 1340, 19%; m/z 1360, 48%, m/z 1378, 98%; m/z 1397, 69%; m/z 1415,29%; m/z 1434, 63%; m/z 1452, 100%; m/z 1470, 69%; m/z 1489, 31%; m/z 1508, 48%; m/z 1526, 67%; m/z 1544, 52%; m/z 1563, 25%; m/z 1582, 29%; m/z 1600, 37%; m/z 1618, 29%, m/z 1637, 17%; m/z 1656, 17%; m/z 1674, 15%.

From the above, the average molecular weight was calculated to be 1463; the ring favoring ratio, calculated using peaks 3D1G and 2D2G, was 1.42.

EXAMPLE 4

Alkylation by epichlorohydrin of alpha-cyclodextrin in refluxing aqueous suspension of calcium hydroxide; high degree of substitution:

The same procedure as described above was used for alpha-cyclodextrin and yielded 7.484 g of the product. Analysis by chromatography documented the absence of polymeric species. Product was detected as a continuous spot from Rf 0.13 to 0.58; alpha-cyclodextrin on the same plate had Rf 0.37.

Mass spectrum of the region of molecular ions of components containing one cyclodextrin ring per molecule was measured in FAB mode. Only attribution of the first five peaks observed is necessary to record, since as above, the attribution of peaks above m/z 1106 is in parallel to that already made. Thus, attribution of the peak at m/z 1142 here corresponds to that of at m/z 1466 made for gamma-cyclodextrin and so on. Results are summarized as follows:

m/z 978, 22%, (alpha-cyclodextrin); m/z 1014, 82%, (matrix); m/z 1394, 18%, (undetermined); m/z 1086, 58%, (2D); m/z 1106, 71%, (1D1G) and (matrix); m/z 1142, 63%; m/z 1160, 100%; m/z 1178, 56%; m/z 1198, 85%; m/z 1216, 77%; m/z 1234, 97%; m/z 1252, 48%; m/z 1272, 28%; m/z 1290, 75%; m/z 1308, 61%; m/z 1326, 34%; m/z 1346, 21%; m/z 1364, 29%; m/z 1382, 43%; m/z 1400, 20%; m/z 1474, 16%.

From the above, the average molecular weight of 1204 was calculated. The ring favoring ratio, calculated using 3D1G and 2D2G peaks, was 0.79.

EXAMPLE 5

Alkylation by epichlorohydrin of gamma-cyclodextrin after gelling its aqueous solution with calcium hydroxide:

Gamma-cyclodextrin (10 g of a hydrate, 55 mmoles of glucopyranosyl residue) was dissolved in water (100 ml) and added to calcium hydroxide (4.63 g, 62.5 mmoles) placed in the container of a ball mill. The resulting suspension was within several minutes transformed into a gel. Epichlorohydrin (8.8 ml (110 mmoles)) and balls of the ball mill were then added and the container was rotated for overnight. During this time the gel was transformed into a thin suspension. Processing similar to that described in Example 1 yielded 8.299 g of the product.

Chromatographic analysis indicated that the product has some species which have several cyclodextrin moieties, but no truly polymeric fraction. The product formed a continuous spot of Rf value between 0.06 to 0.64.

Analysis by mass spectroscopy in FAB mode revealed that, in the molecular ion region of species containing one cyclodextrin ring, there are 30 peaks as follows:

m/z 1409, 16%, (2D); m/z 1427, 10%, (1D1G); m/z 1447, 11%, (2G); m/z 1465, 39%, (3D): m/z 1484, 29%, (2D1G); m/z 1502, 28%, (1D2G); m/z 1522, 72%, (3G) and (4D); m/z 1540, 66%, (3D1G); m/z 1558, 58%, (2D2G); m/z 1578, 75%, (1D3G) and (5D); m/z 1596, 96%, (4G) and (4D1G); m/z 1614, 96%, (3D2G); m/z 1632, 70%, (2D3G) and (6D); m/z 1652, 81%, (1D4G) and (5D1G); m/z 1670, 100%, (5G) and (4D2G); m/z 1688, 88%, (3D3G) and (7D); m/z 1707, 72%, (2D4G) and (6D1G); m/z 1726, 69%, (1D5G) and (5D2G); m/z 1744, 74%, (6G) and (4D3G) and (8D); m/z 1762, 68%, (3D4G) and (7D/G); m/z 1780, 55%, (2D5G) and (6D2G); m/z 1799, 32%, (1D6G) and (5D3G); m/z 1817, 42%, (7G) and (4D4G) and (8D1G); m/z 1836, 40%, (3D5G) and (7D2G); m/z 1855, 33%, (2D6G) and (6D3G); m/z 1875, 28%, (1D7G and (5D4G); m/z 1893, 22%, (8G) and (4D5G) and (8D2G); m/z 1911, 20% (3D6G) and (7D3G); m/z 1931, 18%, (2D7G) and (6D4G); m/z 1948, 13%, (1D8G) and (5D5G).

The average molecular weight was 1669 and half-width of the envelope was about 305. Gamma cyclodextrin was not detected. The ring favoring ratio was calculated using 3D1G and 2D2G peaks and was found to be 0.77. The product was not analyzed for components containing two cyclodextrin rings.

EXAMPLE 6

Alkylation by epichlorohydrin of gamma-cyclodextrin in diluted aqueous solution of sodium hydroxide:

Condensation in which epichlorohydrin was added to a solution of gamma-cyclodextrin in aqueous sodium hydroxide (2.5%) at room temperature yielded product of Rf 0.19–0.47, using methods described above. Distribution in the FAB mass spectrum was bimodal with the most intensive peaks at m/z 1450 (attributed to 2G) and at m/z1672 (attributed to 5G and 4D2G), respectively. The ring favoring ratio was calculated using 3D and 2D1G peaks and was found to be 0.72.

EXAMPLE 7

Alkylation by epichlorohydrin of gamma-cyclodextrin in aqueous solution to which sodium hydroxide was slowly added:

In this preparation a solution of aqueous sodium hydroxide was slowly added (3 hours total) to a rapidly mixed emulsion of epichlorohydrin in aqueous solution of gamma-cyclodextrin (9%). The emulsion cleared in two hours; the product had Rf 0–0.62. FAB mass spectrum in the molecular ion area had monomodal distribution with base peak at m/z 1855 (attributed to 2D6G and 6D3G). The ring favoring ratio could not be calculated unequivocally; substitution was too high to obtain unequivocal results.

EXAMPLE 8

Alkylation by epichlorohydrin of gamma-cyclodextrin performed in presence of in situ formed hydroxides or in presence of buffering salts:

In this preparation epichlorohydrin was added to a gel formed from gamma-cyclodextrin, calcium chloride and sodium hydroxide in water; the product had Rf 0.18–0.47 with stronger colorations at Rf values 0.24, 0.28 and 0.35.

FAB mass spectrum had a monomodal distribution with a base peak in the molecular ion area at m/z 1466 (attributed to 3D). The ring favoring ratio was calculated using 3D1G and 2D2G peaks and was found to be 0.82.

Similar experiments were performed using aluminum chloride, zinc chloride, magnesium chloride or silicic acid in place of calcium chloride; the products were examined by thin layer chromatography and yielded patterns similar to those above.

EXAMPLE 9

Alkylation by 1,2-dichloroethane of gamma-cyclodextrin in refluxing aqueous suspension of calcium hydroxide, without activator:

To a boiling stirred suspension of gamma-cyclodextrin (10 g, 55 mmoles of glucopyranosyl residue) and calcium hydroxide (8.214 g, 111 mmoles) in water (100 ml), 1,2-dichloroethane (8.8 ml, 111 mmoles) was added through a reflux condenser. Refluxing and stirring was continued for 21 hours. The reaction mixture was filtered while hot (upon cooling a gel was formed). The filtrate was dialyzed twice against tap water and once against the distilled water (altogether 15 hours) and, after additional filtration evaporated in vacuo to dryness. The residue was ground to a white powder (6.014 g) of. Chromatographic analysis indicated the presence of two main species—gamma-cyclodextrin of Rf 0.29 and a compound of Rf 0.39, obviously identical to that obtained in the reaction using the activator and described in example 10.

EXAMPLE 10

Alkylation by 1,2-dichloroethane of gamma-cyclodextrin in refluxing aqueous suspension of calcium hydroxide, with activator:

In an attempt to increase the substitution, the experiment was repeated, but potassium iodide (3.686 g, 22 mmoles), which is recommended as an activator in alkylations by alkyl chlorides, was added. The stirring and refluxing lasted for a total of 53 hours; the processing as above yielded 5.025 g of a product.

Chromatographic analysis indicated again the presence of two main components, gamma-cyclodextrin of Rf 0.24 and a compound with Rf 0.34; additionally, five minor components were detected with the following Rf values: 0.11, 0.17, 0.28, 0.40 and 0.47.

Mass spectrum, measured in FAB mode, showed the presence of the following components:

m/z 1298, 96%, (gamma-cyclodextrin); m/z 1324, 63%, (1D); m/z 1336, 71%, (one 2-hydroxyethyl); m/z 1350, 26%, 2D; m/z 1362, 43%, (one 2-chloroethyl) and (1D one 2-hydroxyethyl); m/z 1390, 28%, (two 2-hydroxyethyls); m/z 1432, 19%, (unidentified); m/z 1450, 100%, (one 2-iodoethyl); m/z 1476, 64%, (1D one 2-iodoethyl) and (matrix); m/z 1502, 18%, (2D one 2-iodoethyl).

EXAMPLE 11

Alkylation by 1,2-dichloroethane of beta-cyclodextrin in refluxing aqueous suspension of calcium hydroxide, with activator:

Beta-cyclodextrin was derivatized in the same way as gamma-cyclodextrin in example 10 and yielded 3.419 g of a product as a white powder.

Chromatographic analysis revealed the presence of beta-cyclodextrin (Rf 0.39) and two major components (Rf 0.52 and 0.65) in addition to some minor ones. Mass spectrum, measured in MALDI mode, had in the molecular ion region of components containing one cyclodextrin ring the following peaks:

m/z 1160, 44%, (beta-cyclodextrin); m/z 1175, 34%, (possibly H+ ion of one 2-hydroxyethyl); m/z 1186, 100%, (1D); m/z 1213, 54%, (2D); m/z 1227, 46% (one 2-chloroethyl); m/z 1239, 19%, (3D); m/z 1252, 15%, (2D one 2-hydroxyethyl).

EXAMPLE 12

Alkylation by 1,2-dichloroethane of alpha-cyclodextrin in refluxing aqueous suspension of calcium hydroxide, with activator:

The same potassium iodide activated reaction as in Example 11 was used in derivatization of alpha-cyclodextrin. In this case, the period of refluxing and stirring was 84 hours and yielded 3.922 g of the product as a white powder.

Chromatographic analysis revealed the presence of alpha-cyclodextrin (Rf 0.42) and of a component with Rf 0.51; additionally, a minor component with Rf 0.46 was present.

Mass spectrum, measured in the FAB mode, had the following peaks:

m/z 974, 100%, (alpha-cyclodextrin); m/z 1000, 35%, (1D); m/z 1014, 18%, (one 2-hydroxyethyl) and (matrix); m/z 1066, 18%, (two 2-hydroxyethyls); m/z 1106, 14%, (probably matrix), m/z 1198, 14%, (probably matrix).

EXAMPLE 13

Alkylation by 1,2-dibromopropane of gamma-cyclodextrin in refluxing aqueous suspension of calcium hydroxide:

Gamma-cyclodextrin (10 g, 55 mmoles of glucopyranosyl residue) was condensed with 1,2-dibromopropane (11.6 mL, 111 mmoles) in the same conditions as in Example 12. No activator was used and the period of refluxing was 70 hours. Product was, after grinding, a white powder (2.547 g).

Chromatography analysis revealed the presence of three major components of Rf 0.17, 0.37, 0.44 and one minor one of Rf 0.54 in addition to gamma-cyclodextrin (Rf 0.29).

Mass spectrum, measured in MALDI mode, had the following peaks:

m/z 1322, 100%, (gamma-cyclodextrin), m/z 1362, 76%, (1D); m/z 1379, 30%, (one 2-hydroxypropyl); m/z 1440, 12%, (2D), m/z 1439, 13%, (3D) and (one 2-bromopropyl).

The above product was smoothly permethylated, after the dissolution in anhydrous dimethyl sulfoxide, by the sequential treatment with powdered sodium hydroxide and an excess of methyl iodide. After the decomposition of the reaction mixture by water, the product was extracted into chloroform. The extracts, after drying and evaporation to dryness, yielded the product, a colorless glass.

EXAMPLE 14

Alkylation by 1,2-dichloroethane of alpha-cyclodextrin in organic solvent:

Alpha-cyclodextrin was dehydrated at 120° C. (measured directly in the substance) for about an hour. The dried alpha-cyclodextrin (1.8 g, 11 mmoles) was added to the anhydrous dimethylformamide (20 ml) and the suspension was refluxed and stirred. Calcium hydroxide (1.64 g, 22 mmoles) was then added, followed by 1,2-dichloroethane. (3.5 ml, 48 mmoles). Refluxing and stirring were continued for 12 hours. The suspension was then filtered giving a brown colored solution. After the evaporation to dryness in vacuo, the residue was dissolved in the solution of water (20 ml) and acetic acid (2 ml); active carbon and cellulose powder were then added and the suspension was processed as above. Evaporation yielded a glassy residue, which was ground to a brown powder (0.495 g).

Chromatographic analysis revealed the presence of alpha-cyclodextrin (Rf 0.37) and of the same component as obtained when an aqueous medium was used (Rf 0.53). Additionally, there were several minor components with lower Rf values.

EXAMPLE 15

Alkylation by methyl iodide of gamma-cyclodextrin in refluxing aqueous suspension of calcium hydroxide:
Gamma-cyclodextrin (10 g, 55 mmoles of glucopyranosyl residue) and calcium hydroxide (4.11 g, 55.5 mmoles) were added to water (100 ml) and the suspension was heated and stirred under reflux condenser. The suspension was transformed into a gel, which again liquefied by heating. Methyl iodide (6.9 ml, 111 mmoles) was added through the reflux condenser drop-wise while boiling was continued. Addition required an hour; boiling and stirring continued for another two hours and then the mixture was left standing overnight. The processing of the mixture by filtrations and dialysis as described in the examples above yielded 6.701 g of white material. Cyclodextrins substituted by alkyl substituents are known to be very well separated by the chromatographic system used according the number of substituents. Six components were distinctly detected—from the unsubstituted gamma-cyclodextrin to a pentamethyl species; respective Rf values were 0.29, 0.35, 0.44, 0.52, 0.61, 0.70. The strongest spots were those of monomethyl and dimethyl gamma-cyclodextrins. These results show that reaction of gamma-cyclodextrin with methyl iodide is distinctly slower than that with epichlorohydrin.

EXAMPLE 16

Alkylation by 3-chloro-2-methylpropene of gamma-cyclodextrin in refluxing aqueous suspension of calcium hydroxide:

Gamma-cyclodextrin (10 g, 111 mmoles of glucopyranosyl residue) was alkylated with this reagent in the same conditions as Example 15, but 16 hours of reflux were used; 7.721 g of white powder (after grinding) was obtained. Chromatography analysis revealed components with the following Rf values: 0.29 (gamma-cyclodextrin); 0.49 and 0.54 (monosubstituted product); 0.67 (disubstituted product).

EXAMPLE 17

Alkylation by diethylaminoethyl chloride of gamma-cyclodextrin after gelling its aqueous solution with calcium hydroxide:

To a suspension of calcium hydroxide in water (30 ml) in a ball mill container, a hot aqueous solution (30 ml) of gamma-cyclodextrin (10 g, 111 mmoles of glucopyranosyl residue) was added. After a gel was formed, a solution of diethylaminoethyl chloride hydrochloride (15.65 g, 91 mmoles) in water (40 ml) and mill balls were added and the rotation started. After one hour of rotation, the gel liquefied; rotation continued for another 12 hours. The processing by filtration, dialysis and evaporation yielded 8,555 g of slightly yellow glassy material.

Chromatographic analysis revealed that the product contains mainly components with Rf from 0 to 0.14 with minor ones extending up to 0.3.

Mass spectrum, measured in FAB mode, contained a large number of peaks, which after an analysis, revealed that the expected series of mono- to undeca-derivatives. Each of these components appeared in the mass spectrum as several species differing by the degree of neutralization. No peak for gamma-cyclodextrin was detected. From the many peaks observed, just the most prominent are given below:

m/z 1495, 38%, (two diethylaminoethyls); m/z 1595, 51%, (three diethylaminoethyls); m/z 1730, 58%, (four diethylaminoethyls one chloride), m/z 1829, 100%, (five diethylaminoethyls one chloride): m/z 1927, 79%, (six diethylaminoethyls one chloride), m/z 2064, 93%, (seven diethylaminoethyls two chlorides), m/z 2162, 69%, (eight diethylaminoethyls two chlorides), m/z 2299, 68%, (nine diethylaminoethyls three chlorides); m/z 2434, 53%, (ten diethylaminoethyl four chlorides), m/z 2534, 35%, (eleven diethylaminoethyls four chlorides).

The average degree of substitution calculated from the above data is close to 6.5 substituents per molecule.

EXAMPLE 18

Alkylation by 1,3-propanesultone of gamma-cyclodextrin after gelling its aqueous solution with calcium hydroxide:

The experiment was performed as described in Example 17, but 1,3-propanesultone (11.087 g, 91 mmoles) was used instead of diethylaminoethyl chloride and before the dialysis sodium sulfate (19.88 g, 140 mmoles) was added to help to exchange calcium for sodium ions. The product, a white powder after grinding, amounted to 10.856 g.

Chromatographic analysis showed that there was no gamma-cyclodextrin in the product, which had a continuous spot of Rf 0.03–0.28.

Mass spectrum was measured in MALDI mode. No peak which can be attributed to gamma-cyclodextrin was present. The peaks recorded below correspond to the sodium ion of gamma-cyclodextrin substituted with the increasing number of $C_3H_6O_3SNa$ substituents, denoted below as sulfonates:

m/z 1464,32%, (one sulfonate); m/z 1607, 46%, (two sulfonates), m/z 1751, 42%, (three sulfonates), m/z 1895, 96%, (four sulfonates); m/z 2039, 100%, (five sulfonates); m/z 2183, 54%, (six sulfonates); m/z 2327, 22%, (seven sulfonates), m/z 2471, 16%, (eight sulfonates).

From the above data, the average degree of substitution was calculated to be 4.5 per molecule.

EXAMPLE 19

Preparation of partially acetylated cyclodextrins by acetylation in an aqueous suspension of calcium hudroxide or by hydroysis of fully acetylated cyclodextrin in calcium hudroxide:

To a stirred solution of alpha-cyclodextrin (5 g, 27 mmoles of glucopyranosyl residue) in hot water (16 ml), calcium hydroxide (8.15 g, 110 mmoles) was added. The suspension was placed into an ice bath. After a stiff gel was formed, acetanhydride (12.2 ml, 110 mmoles). The flask was shaken vigorously. An exothermic reaction occurred in which the contents of the flask was converted to a powdery solid. Ice was added to the flask. The powder dissolved to provide a resulting solution having a pH 6. The solution was then extracted with chloroform (25 ml), dialized against cold water for two hours, treated with deionizing resin, filtered and evaporated in vacuo. The resulting residue was ground to a white powder (6.04 g), which, by chromatographic analysis, was shown to contain some alpha-cyclodextrin (Rf 0.33) and its partial acetates with a lower degree of substitution (Rf 0.41–0.65). Drying and evaporation of chloroform extracts yielded partial acetates of alpha-cyclodextrin with a higher degree of substitution (85 mg) of Rf 0.65–0.79. The fully acetylated cycloedextrins have Rf 0.85–0.9. The polydisperse distribution of the product is probably due to the hydrolysis during the isolation.

Partial acetates of cyclodextrin are rapidly hydrolyzed by water. A mixture of partially acetylated beta-cyclodextrin, made by melting fully acetylated beta-cyclodextrin with calcium hycroxide, lost about half of its actyl groups by overnight treatment with water at room temperature.

EXAMPLE 20

Preparation of cyclodextrin derivatives with rigidly extended cavity by two-step procedure:

A mixture of gamma-cyclodextrin derivatives (2 g) carrying 2-methylpropen-3-yl substituents, prepared as described in Example 16, was added while stirring to trifluoroacetic acid (10 ml). After completion of the dissolution, the solution was left standing for a day, then evaporated to dryness in vacuo and kept on boiling water bath for couple of minutes afterward. The residue was treated with concentrated aqueous ammonia (10 ml), evaporated to dryness again and dissolved in water. Small molecular weight components were removed by dialysis against water and the solution filtered and again evaporated to dryness. The residue was ground to a white powder (0.81 g), in which, as established by chromatography analysis, there were no starting components carrying 2-methylpropen-3-yl substituents present. Their conversion, through intramolecular cyclization to 2,2-dimethyl-1,4- dioxane residues, may be assumed to occur.

EXAMPLE 21

Preparation of resins containing cyclodextrin derivatives with rigidly extended cavity:

The water soluble derivative of beta-cyclodextrin containing 1,4-dioxane fused rings, preparation of which was described in Example 2, was converted into a water insoluble resin as follows: To a stirred and heated (90° C.) solution of detergent (Triton×100, about 0.5 g) in toluene was added a solution of the cyclodextrin derivative (0.5 g) and sodium hydroxide (0.1 g) in warm water (1 ml). Heating was continued for another hour. After cooling to room temperature, toluene was decanted from the product which adhered as a crust to the walls of the container. After the extensive washing of the crust with methanol, acetone and water and drying, a glassy solid (0.422 g) was obtained which could be easily disintegrated by a spatula into a powder.

EXAMPLE 22

Solubilization and Stabilization of compounds of low water solubility with cyclodextrin derivatives:

A compound of low solubility in water is suspended in water or in an aqueous solution. Cyclodextrin derivative is added in about ten times the weight of the compound to be solubilized and the suspension or emulsion is agitated for at least a day. Thereafter the undissolved material is removed by filtration or centrifugation yielding a clear solution of a complex of the compound with the cyclodextrin derivative. If the complex is desired in a solid form, water is removed by freeze drying or evaporation.

It should be realized that cyclodextrin complexes are formed and dissociated very rapidly—usually in a fraction of a second. The slow step in the dissolution process is the transfer of the poorly soluble compound from its solid phase into the aqueous phase. The subsequent formation of the cyclodextrin complex occurs instantly. Consequently, the process can be accelerated by steps which accelerate solubilization of the molecule which is to be complexed. Such a step may be, for example, brief heating of the suspension. Dissolution may also be facilitated by addition of volatile organic solvents, acids or bases to the aqueous suspension which, after assisting in solubilization in the aqueous phase, can be removed by evaporation.

Absorption of lipophilic substances from the aqueous solution by water-insoluble cyclodextrin resins can be accomplished by a simple filtration through a layer of resin.

I claim:

1. A composition comprising cyclodextrins wherein at least 10% of the cyclodextrin molecules have a dioxane ring fused to a glucopyranosyl residue.

2. A composition of claim 1 wherein 30% to 60% of the cyclodextrin molecules contain a dioxane ring.

3. A composition of claim 1 wherein at least 50% of the cyclodextrin molecules contain a dioxane ring.

4. A composition of claim 1 wherein dioxane substituents consist of at least one of 1,4-dioxane, 2-methyl-1,4-dioxane, 2-hydroxymethyl-1,4-dioxane or 2,2-methyl-1,4-dioxane fused to the 2- and 3- positions of the glucopyranosyl residues.

5. A water-insoluble resin containing cross-linked cyclodextrins having dioxane substituents on the glucopyranosyl residues.

* * * * *